United States Patent
Dietz et al.

(10) Patent No.: US 9,847,552 B2
(45) Date of Patent: Dec. 19, 2017

(54) METHOD FOR PRODUCING LOW-ACID LITHIUM BORATE SALTS AND MIXTURES OF LOW-ACID LITHIUM BORATE SALTS AND LITHIUM HYDRIDE

(71) Applicant: Chemetall GmbH, Frankfurt (DE)

(72) Inventors: Rainer Dietz, Egelsbach (DE); Ulrich J. Wietelmann, Friedrichsdorf (DE); Uwe Lischka, Frankfurt (DE); Ute Emmel, Frankfurt (DE)

(73) Assignee: ALBERMARLE GERMANY GMBH, Frankfurt am Main (DE)

( * ) Notice: Subject to any disclaimer, the term of this patent is extended or adjusted under 35 U.S.C. 154(b) by 265 days.

(21) Appl. No.: 14/815,371

(22) Filed: Jul. 31, 2015

(65) Prior Publication Data
US 2016/0028120 A1   Jan. 28, 2016

Related U.S. Application Data

(63) Continuation of application No. 12/667,550, filed as application No. PCT/EP2008/058599 on Jul. 3, 2008, now abandoned.

(30) Foreign Application Priority Data

Jul. 4, 2007 (DE) .................. 10 2007 031 199

(51) Int. Cl.
H01M 10/0567 (2010.01)
H01M 10/0569 (2010.01)
C07F 5/02 (2006.01)
H01M 10/052 (2010.01)
H01M 10/0568 (2010.01)

(52) U.S. Cl.
CPC ......... H01M 10/0567 (2013.01); C07F 5/022 (2013.01); H01M 10/052 (2013.01); H01M 10/0568 (2013.01); H01M 10/0569 (2013.01); H01M 2300/0025 (2013.01); H01M 2300/0034 (2013.01); H01M 2300/0091 (2013.01)

(58) Field of Classification Search
CPC .......... H01M 10/052; H01M 10/0567; H01M 10/0568; H01M 10/0569; H01M 2300/0025; H01M 2300/0034; H01M 2300/0091
See application file for complete search history.

(56) References Cited

U.S. PATENT DOCUMENTS

| | | |
|---|---|---|
| 6,506,516 B1 | 1/2003 | Wietelmann et al. |
| 7,172,834 B1 | 2/2007 | Jow et al. |
| 7,226,704 B2 | 6/2007 | Panitz et al. |
| 7,666,310 B2 | 2/2010 | Wietelmann et al. |
| 7,674,911 B2 | 3/2010 | Wietelmann et al. |
| 7,727,669 B2 | 6/2010 | Deng et al. |
| 7,867,294 B2 | 1/2011 | Deng et al. |
| 2004/0063986 A1* | 4/2004 | Wietelmann ............ C07F 5/022 558/290 |
| 2004/0076887 A1 | 4/2004 | Panitz et al. |
| 2004/0096746 A1 | 5/2004 | Wietelmann et al. |
| 2006/0138056 A1 | 6/2006 | Wietelmann et al. |
| 2006/0269844 A1 | 11/2006 | Deng et al. |

FOREIGN PATENT DOCUMENTS

| | | |
|---|---|---|
| DE | 198 29 030 C1 | 10/1999 |
| DE | 100 49 097 A1 | 4/2002 |
| DE | 101 08 608 A1 | 9/2002 |
| DE | 102 09 429 A1 | 9/2002 |
| WO | 02/28500 A1 | 4/2002 |

OTHER PUBLICATIONS

Bessler, et al. "Borkomplexe mit Dicarbonsaeuren: Bix(oxalato)borate und Bis(malonato)borate" (with English translation—"Boron Complexes with Dicarboxylic Acids: Bis(oxalato) borates and bis(malonato)borates"), Z. Natursforsch., 87b (1982), pp. 1020-1025.

Xu, et al. "Electrochemical impedance study of graphite/electrolyte interface formed in LiBOB/PC electrolyte", J. of Power Sources, 143 (2005), pp. 197-202.

Xu, et al. "LiBOB: Is it an alternative salt for lithium ion chemistry?", J. of Power Sources, 146 (2005), pp. 79-85.

Panitz, et al. "Film formation in LiBOB-containing electrolytes", J. of Power Sources, 153 (2006), pp. 396-400.

* cited by examiner

*Primary Examiner* — Carlos Barcena

(57) ABSTRACT

A solvent-free mixture of a crude lithium borate salt and lithium hydride, wherein the lithium hydride is at least 0.001 wt. % and at most 10 wt. %, relative to the weight of crude lithium borate salt, wherein the mixture has a water content of at most 100 μmol/g and an acid content of at most 10 μmol $H^+$/g of crude lithium borate salt, method for producing the same, and use thereof for battery electrolytes.

15 Claims, 1 Drawing Sheet

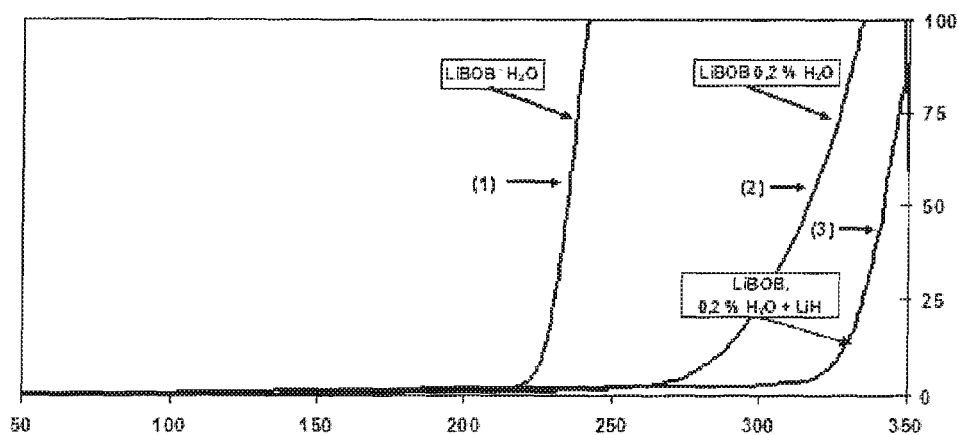

METHOD FOR PRODUCING LOW-ACID LITHIUM BORATE SALTS AND MIXTURES OF LOW-ACID LITHIUM BORATE SALTS AND LITHIUM HYDRIDE

FIELD OF THE INVENTION

The invention provides a process for producing low-acid lithium borate salts for applications in battery electrolytes.

BACKGROUND OF THE INVENTION

Lithium batteries have become established as energy stores above all for applications in portable electronics (laptops, mobile telephones), because of their high energy density and power density in comparison to other battery types. A distinction is made between primary lithium batteries, which are non-rechargeable batteries having mostly lithium metal anodes, and secondary systems, in other words rechargeable batteries.

Both battery types contain anhydrous liquid or gel-like ion-conductive electrolytes, in which supporting electrolytes, for example $LiPF_6$, $LiBF_4$, lithium imides, lithium methides or lithium borate salts, for example lithium bis(oxalato)borate (LiBOB, corresponding to $Li[B(C_2O_4)_2]$), are present in dissolved form.

In comparison to lithium element fluorides such as $LiPF_6$ or $LiBF_4$, lithium borate salts such as LiBOB bring about a significant improvement in cycle stability and safety properties in secondary lithium batteries (Cox, S. S. Zhang, U. Lee, J. L. Allen, T. R. Jow, J. Power Sources 46, 2005, 79-85). This is due to a modified form of protective coating formation on the carbon anode of a lithium battery: borate electrolytes give rise to the formation of a thin, very stable $Li^+$-conductive coating on this anode, which is stable even at elevated temperatures and thus prevents dangerous decomposition reactions between the charged anode and the electrolyte, for example (J.-C. Panitz, U. Wietelmann, M. Wachtler, S. Ströbele, M. Wohlfahrt-Mehrens, J. Power Sources 153, 2006, 396-401; Chemetall brochure 2005). The improvements to the protective coating brought about by borate salts offer users new possibilities for electrolyte formulation. For instance, the difficult-to-handle ethylene carbonate (1,3-dioxolan-2-one), for example, can be abandoned in favour of propylene carbonate (4-methyl-1,3-dioxolan-2-one) (K. Xu, S. Zhang, R. Jow, J. Power Sources 143, 2005, 197-202).

Lithium borate salts for example having the general formulae I or II are used:

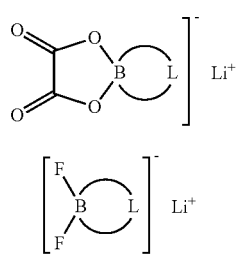

L is a chelating agent having two terminal oxygen atoms with the general formula

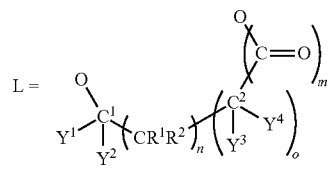

wherein:

$Y^1$ and $Y^2$ together denote O, where m=0 or 1, n=0 or 1, o=0 and $R^1$ and $R^2$ independently of one another denote H, F, Cl, Br, OR (R=alkyl) or R' (alkyl), or $Y^1$, $Y^2$, $Y^3$, $Y^4$ independently of one another each denote OR (R=alkyl), H, F, Cl, Br, R (alkyl), where m=0 or 1, n=0, o=1, or $Y^1$, $C^1$, $Y^3$ and $C^2$ are members of a 5- or 6-membered aromatic or heteroaromatic ring (with N, O or S as heteroelement), which can optionally be substituted with alkyl, alkoxy, carboxy or nitrile, wherein $Y^2$ and $Y^4$ are omitted, with n=0 and m=0 or 1, o=1.

Lithium borate salts are generally produced by reacting an oxidic boron compound (for example boric acid, boron oxide or a boric acid ester) with oxalic acid or an oxalic acid salt or a fluoride donor, for example $BF_3$, and optionally further dihydroxy compounds, for example dicarboxyl compounds, diphenols, and a lithium raw material, for example lithium carbonate, lithium hydroxide, lithium alcoholate or similar.

The commonest method of producing bis(chelato)borates of type I involves suspending the components in a solvent and separating off the water azeotropically (E. Bessler and J. Weidlein, Z. Naturforsch. 37b, 1020-1025, 1982).

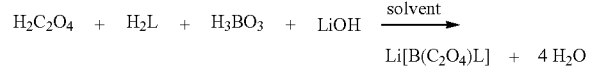

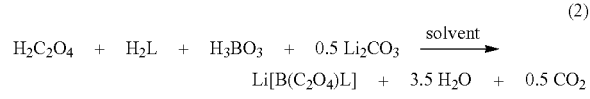

Suitable solvents are those which form an azeotrope with water, for example saturated or aromatic solvents such as heptane, octane, toluene or cumene.

In a variant the alkali metal can also be incorporated via the lithium salt of the ligand (LiHL or $Li_2L$) or a metal borate, for example $LiBO_2$, for example:

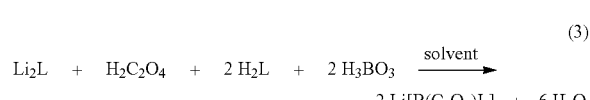

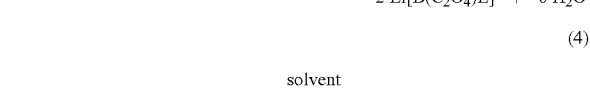

A further production possibility is to react a metal tetraalkoxyborate $M[B(OR)_4]$ with two equivalents of the ligands in an organic solvent (DE-C-19829030), for example:

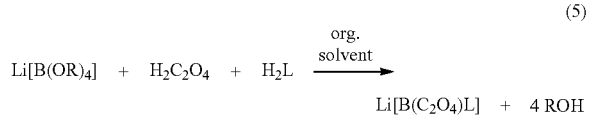

(5)

where R is an alkyl radical, for example $H_3C$ or $C_2H_5$.

The alcohol itself (formed in the reaction, ROH), for example methanol or ethanol, or an aprotic, polar solvent, for example acetonitrile, can be used as the organic solvent.

Finally, the production of LiBOB in homogeneous aqueous solution by reaction according to (1), (2), (3) or (4) and isolation in solid, anhydrous form after total evaporation and vacuum drying is known. The disadvantage of this process is that the space-time yield is relatively low. For instance, in DE-C-19829030, Example 1, only 185 g of product are obtained from approx. 3.1 kg of reaction solution.

DE-A-10108608 discloses the synthesis of alkali metal bis(chelato)borates by means of the reactions listed above without addition of solvents in the heterogeneous phase and removal of the water formed during the reaction. This process has the disadvantage of relatively poor drying results. For instance, DEA-10108608, Example 1, discloses a product having a water content of 0.4%. This water content is well above the values required for supporting electrolytes for batteries.

Compounds having the general formula II can be produced by reacting boron trifluoride with lithium salts. For example, lithium difluorooxalatoborate (LiDFOB) is produced by reacting $BF_3 \cdot Et_2O$ (a complex of boron trifluoride with diethyl ether as solvate) and $Li_2C_2O_4$ (S. S. Zhang, Electrochem. Commun. 8 (2000, 1423-1428):

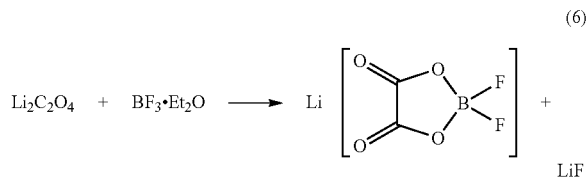

(6)

Many supporting electrolytes decompose more or less quickly in the presence of protic compounds such as water, in the following manner for example:

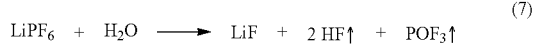

(7)

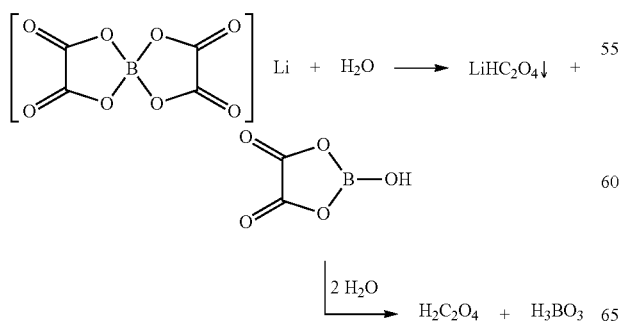

(8)

The gaseous products formed during the hydrolysis of fluorine-containing supporting electrolytes, for example HF and $POF_3$, are highly caustic and damaging to the other battery components, for example the cathode materials. Thus HF leads to the disintegration of manganese spinels, for example, and destroys the top coating on the electrode materials, which is important for a long operating life. The cycle stability of secondary batteries is impaired as a consequence. Borate electrolytes are also sensitive to water. In this case hydrolysis products, some of them insoluble, are formed, which likewise impair the functional properties of the batteries. Hydrolysis products such as boric acid or oxalic acid are acid-corrosive and similarly impair the formation of the top coating on the cathode or anode materials.

It is therefore essential to use products with the lowest possible water and acid contents for the production of battery electrolytes if batteries having long-term cycle stability are required.

The removal of water and/or acids can take place at the liquid electrolyte stage. DE-A-10049097 discloses the separation of water and protic contaminants from an organic liquid electrolyte by bringing it into contact with insoluble alkali-metal hydrides and separating off the insoluble secondary reaction products. The disadvantage of the process described is that the drying times are relatively long and the amounts of drying agent to be used are very high; thus approx. 0.4 to 6 g of lithium hydride are used per kg of electrolyte solution, corresponding to about 2 to 25 g per kg of lithium borate salt content.

In order to keep the amount of purification work at the end of the electrolyte production process as low as possible, it is necessary to use a lithium borate salt which is already largely dry and free from acid.

OBJECTS OF THE INVENTION

The object of the present invention is to provide a simple, cost-effective process for producing anhydrous and acid-free (or low-water and low-acid) solid lithium borate salts and solutions thereof in aprotic organic solvents.

SUMMARY OF THE INVENTION

Surprisingly, the object is achieved by mixing crude lithium borate salts contaminated with water and/or acid, abbreviated below to crude lithium borate salt, in the solid phase or suspended in a solvent which does not dissolve the crude lithium borate salt, with lithium hydride and stirring them together, preferably at elevated temperature. This treatment preferably takes place either under vacuum or in a dry atmosphere, most particularly preferably in an inert-gas atmosphere. The compounds represented by the generic formulae I and II are used as lithium borate salts:

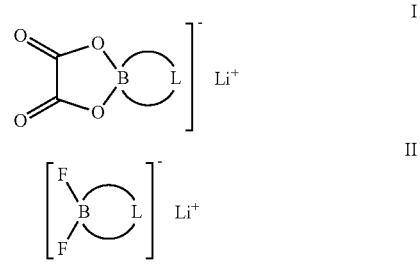

L is a chelating agent having two terminal oxygen atoms with the general formula

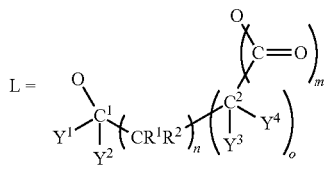

wherein
- $Y^1$ and $Y^2$ together denote O, where m=0 or 1, n=0 or 1, o=0 and $R^1$ and $R^2$ independently of one another denote H, F, Cl, Br, OR (R=alkyl) or R' (alkyl), or
- $Y^1, Y^2, Y^3, Y^4$ independently of one another each denote OR (R=alkyl), H, F, Cl, Br, R' (alkyl), where m=0 or 1, n=0, o=1, or
- $Y^1, C^1, Y^3$ and $C^2$ are members of a 5- or 6-membered aromatic or heteroaromatic ring (with N, O or S as heteroelement), which can optionally be substituted with alkyl, alkoxy, carboxy or nitrile, wherein $Y^2$ and $Y^4$ are omitted, with n=0 and m=0 or 1, o=1.

Particularly preferred are: lithium bis(oxalato)borate (LiBOB), lithium malonato-oxalatoborate (LiMOB), lithium glycolato-oxalatoborate (LiGOB), lithium salicylato-oxalatoborate (LiSOB), lithium lactato-oxalatoborate (LiLOB), lithium catecholato-oxalatoborate (LiBZOB), lithium difluorooxalatoborate (LiDFOB), lithium difluoromalonatoborate, lithium difluoroglycolatoborate, lithium difluoro-salicylatoborate, lithium difluorolactatoborate, lithium difluorocatecholatoborate.

DETAILED DESCRIPTION

The lithium hydride is particularly preferably used in finely dispersed form, i.e. ground. The average particle size $D_{50}$ is preferably 100 μm or below.

Surprisingly it was found that the reducing agent LiH does not react with the lithium borate salt, even at high temperatures.

This is illustrated by way of example by the behaviour of a special lithium borate salt having structure I, lithium bis(oxalato)borate (LiBOB). The diagram in the drawing shows the thermal stability of pure LiBOB contaminated with approx. 0.2% water, LiBOB monohydrate and LiBOB (0.2% water) mixed with 5 wt. % of ground LiH. The experiments were performed in closed steel vessels having a volume of approx. 5 ml.

The diagram in the attached drawing shows pressure build up during thermolysis of various LiBOB grades in closed vessels.

LiBOB undergoes thermal decomposition with formation of gases as follows:

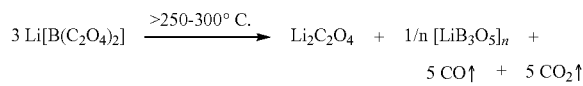

giving rise in closed equipment to a corresponding pressure buildup. The decomposition process is accelerated in the presence of water. The progress of the pressure build-up in closed vessels thus mirrors the progress of the thermal decomposition of the lithium borate salt. It can be seen from the top curves that LiBOB monohydrate decomposes at the lowest temperature (approx. 230° C.). LiBOB slightly contaminated with water begins to build up pressure above about 270° C.

Unexpectedly, however, when mixed with lithium hydride, decomposition begins only at temperatures 50 to 60° C. higher. The expected reduction of the carbonyl groups by the hydride surprisingly does not take place. Furthermore, various analytical methods (ion chromatography, NMR spectroscopy, etc.) identify no substances which might indicate an attack by LiH on the BOB anion.

The mixing of lithium borate salt and lithium hydride can take place in pure form or with addition of an aprotic solvent or solvent blend which does not dissolve the lithium borate salt, with a boiling point or range of at least 100° C. under normal pressure (referred to below as aprotic solvent). The aprotic solvent preferably boils in the range between 110 and 280° C. Suitable aprotic solvents are aromatic or saturated hydrocarbons, perfluorinated or partially fluorinated hydrocarbons or dialkyl ethers. Examples of aromatic hydrocarbons are: toluene, ethyl benzene, xylenes, cumene; examples of saturated hydrocarbons: heptane, octane, nonane, decane, undecane and dodecane and mixtures thereof. Most particularly suitable too are commercially obtainable hydrocarbon blends such as for example Shellsol D70 or D100 or Halpasols. Examples of fluorinated hydrocarbons are: perfluoro(methyldecalin), perfluorononane, perfluorooctane, perfluorotridecane, perfluorodecalin or commercially obtainable perfluorocarbon blends such as perfluorokerosene with a boiling range between 210 and 240° C.

High-boiling dialkyl ethers such as dibutyl ether, diamyl ether or diphenyl ether or mixtures thereof are also suitable.

The amount of lithium hydride to be used is governed by the concentration of protic contaminants in the crude lithium borate salt. As a general rule, a minimum of 0.001 wt. % and a maximum of 10 wt. %, relative to the weight of lithium borate salt used, should be used. The preferred amount of LiH is between 0.01 and 1 wt. %.

The reaction between lithium borate salt and lithium hydride in the absence of an aprotic solvent or solvent blend takes place under an inert-gas atmosphere or under vacuum at temperatures of between 40 and 28° C., particularly preferably under pressures of less than 50 mbar and at temperatures of between 110 and 220° C. The duration of the reaction is between 10 min and 24 hours, preferably between 0.5 and 10 hours.

In the presence of an aprotic solvent which does not dissolve the lithium borate salt, drying and neutralisation preferably take place at a temperature at which the solvent boils. The boiling process brings about an acceleration of the drying process through cavitation effects. Moreover, the aprotic solvents used for the process according to the invention form azeotropic mixtures with water, i.e. water that is present forms a low-boiling-point mixture with the solvent.

Water and aprotic solvent separate in the condensate. The water phase can be separated off using suitable prior art apparatus so that only the aprotic solvent returns to the lithium borate salt/LiH/aprotic solvent blend. A most particularly efficient drying can take place in this way.

The necessary drying times in the presence of an aprotic solvent which does not dissolve the lithium borate salt are dependent on the drying temperature, the amount of lithium hydride used, etc. The concentration of lithium hydride, relative to the weight of crude lithium borate salt, is at least 0.001 and at most 10 wt. % and the concentration of solids (i.e. lithium borate salt and lithium hydride) in the solvent is at least 5 and at most 95% in total.

If drying is carried out in the preferred temperature range of between 110 and 220° C., 0.5 to 10 hours are generally found to be sufficient.

At the end of the drying and neutralisation process the aprotic solvent is removed from the lithium borate salt/lithium hydride mixture. This can take place either via a mechanical liquid/solid separation operation, for example filtration or decanting, or alternatively by means of total evaporation. In total evaporation the condensate is discharged from the distillation apparatus rather than being returned to the distillation vessel. This process can take place under normal pressure or reduced pressure. It is particularly preferable for the final drying to lower the pressure. The final pressure is preferably less than 100 mbar. In this way the aprotic solvent can be removed particularly completely from the lithium borate salt/LiH mixture.

After the drying and neutralisation operation, mixtures of solids are present which are contaminated with excess lithium hydride and reaction products thereof (LiOH, $Li_2CO_3$, $Li_2C_2O_4$). They contain a maximum of 100 μmol of water and a maximum of 10 μmol of $H^+$ per g of crude lithium borate salt. As such mixtures cannot be used directly as supporting electrolytes for lithium batteries, a further object is to separate the cited contaminants from the lithium borate salt. This is achieved most simply through a selective dissolution process. Whereas lithium borate salts generally have a high solubility in many aprotic, polar solvents, the contaminants are scarcely soluble or not at all soluble in the same solvents.

To this end the crude lithium borate salt dried and neutralised according to the invention, hereinafter simply called the crude salt according to the invention, is brought into contact with a likewise aprotic anhydrous and acid-free solvent or solvent blend which dissolves the crude salt well. Ethers, ketones, carbonic acid esters, γ-lactones, carboxylic acid esters and nitriles, either in pure form or blended with one another or mixed with a hydrocarbon, e.g. toluene, ethyl benzene or methyl cyclohexane, are suitable as such crude-salt-dissolving aprotic solvents. Carbonic acid esters, in particular cyclic carbonates such as ethylene carbonate (EC), propylene carbonate (PC), butylene carbonate (BC) and the like, nitriles such as acetonitrile and propionitrile and γ-lactones such as γ-butyrolactone and γ-valerolactone, are most particularly suitable.

Depending on the individual solubility, the concentration of the dissolved crude lithium borate salt is 1 to 50%, preferably 5 to 30%. It was found that the contamination with water is at most 100 μmol/g and that with acids ($H^+$) is at most 10 μmol/g of dissolved crude lithium borate salt.

The process according to the invention is described below by way of example, without the description being intended to limit the scope to a specific crude lithium borate salt or to a specific process.

LiBOB is used as a representative of a lithium borate salt. Crude LiBOB produced according to the prior art typically contains 0.1 to 0.2% water and has a relatively high acid content of >100 μmol/g. The acid content is titrated using a specific method in the anhydrous medium (titration with tertiary amines against bromophenol blue as indicator).

0.1 to 0.5% lithium hydride powder is preferably added to the crude LiBOB and the mixture is then heated with intensive thorough mixing. This operation particularly preferably takes place in the presence of aliphatic hydrocarbons having a boiling range between 110 and 280° C. at temperatures of between 110 and 220° C. The dried and neutralised crude salt isolated from this process either by total evaporation or by a solid/liquid separation process is then introduced with exclusion of air and water, i.e. under vacuum or under an inert-gas atmosphere, into an aprotic solvent which dissolves LiBOB well, preferably ethylene carbonate, propylene carbonate or butylene carbonate, to produce an approx. 10 to 20% solution. The dissolving process can be accelerated by stirring and/or heating. In a stirred system the dissolving process is completed after a few minutes to approx. 5 hours.

In a particular embodiment of the process according to the invention the crude salt solution containing undissolved residues is then stirred at elevated temperatures, for example at 50 to 200° C., for around 10 minutes to 10 hours. Any remaining traces of water and acid introduced with the aprotic solvent and/or the crude lithium borate salt are removed or neutralised by this measure.

The turbid solution treated as described above is then filtered, decanted or centrifuged according to the prior art to separate the sediment. Membrane filtration using filter media having pore diameters of less than 0.5 μm is most particularly preferred.

If for the purification process described solvents are used such as are used in lithium batteries, no further purification and separation operations are generally necessary.

The product solution can be mixed in this form with other components, in other words solvents, lithium salts (e.g. $LiPF_6$) or special additives (e.g. film-forming substances such as vinylene carbonate or redox shuttle molecules such as for example 1,2-divinyl furoate, 1,3-butadiene carbonate or 2-tert-butyl anisole) and then used as a battery electrolyte. It is a different matter if solvents such as for example acetonitrile or butyl acetate, which are not commonly found in batteries, are used for the separation process.

In this case the solvent must either be removed by total evaporation or the dissolved lithium borate salt must be isolated by crystallisation (displacement, evaporative or cooling crystallisation).

It was found that even the solid lithium borate products isolated from the anhydrous and acid-free solutions are generated with much lower water and acid contents than is the case if crude lithium borate salts not pre-treated according to the invention are used. The various aspects of the invention are illustrated by reference to the examples below, without being restricted thereto.

Example 1: Drying and Neutralisation of LiBOB with Lithium Hydride in Halpasol Under Reflux Conditions 1.18 kg of crude LiBOB having a water content of 800 ppm and 1.9 g of LiH powder in 2.9 kg of "Halpasol 166-170" were suspended in a 5-liter vertical dryer with reflux divider, condenser and discharge means for the aqueous phase in the condensate. The heat transfer oil temperature was set to 205° C. and the mixture was refluxed for 1 h (boiling temperature 165 to 167° C.). 0.5 ml of water separated out. After refluxing for a further 1.5 h the reflux divider was switched from reflux to distillation.

Once the bulk of the solvent had condensed, the pressure was gradually reduced, ending at 15 mbar.

The remaining colourless, dry crystallisate was discharged whilst still hot into an inerted, i.e. dried and filled with protective gas, glass flask.

Yield: 1.16 kg LiBOB
Acid content: 2.5 μmol H+/g LiBOB (titration with triethylamine against bromophenol blue in propylene carbonate solution)
Water content: 219 ppm (corresponding to 12 μmol/g LiBOB)
Insoluble proportion: 1.3 wt. % (in acetonitrile)

Example 2: Production of a Clear, Dry and Low-Acid Solution of LiBOB in Propylene Carbonate (PC)

263 g of LiBOB/LiH mixture from Example 1 were introduced into 1380 g of dry PC (water content 30 ppm), which had been placed in an inerted 2-liter double-jacketed reactor. Then the stirred turbid mixture was stirred for 3 hours at 120° C. under an argon blanket. After cooling to room temperature the solution was filtered through a membrane filter supplied by Curio (SCF nylon, pore size 100 nm).
Resulting weight: 1429 g (87% of theoretical) of a clear, yellowish solution. The solution proves to be stable in storage, i.e. no post-precipitation occurs when stored for several months.
Li$^+$: 0.81 mmol/g (corresponding to 15.7 LiBOB)
Acid content: 2.0 μmol H$^+$/g LiBOB content
Water content: 235 ppm (corresponding to 82 μmol/g LiBOB content)

Example 3: Production of Pure, Low-Water and Low-Acid LiBOB Crystallisate by Evaporative Crystallisation in Propylene Carbonate 1186 g of the clear LiBOB solution from Example 2 were crystallised in a 0.5-liter double-jacketed reactor fitted with pitched-blade turbine, distillate divider and jacketed-coil condenser.
To this end 500 ml of the clear solution were first introduced into the reactor, which had previously been dried and filled with argon. Then the reactor was evacuated to a pressure of 10 mbar and the heating jacket temperature adjusted to 150 to 155° C. within 60 min. The reactor contents boiled under these conditions and the discharged distillate was continuously replaced by further fresh solution. 971 g of PC were condensed off in total. Then the vacuum was broken, the reactor cooled to 120° C. and the suspension formed discharged onto a reverse-flow sintered-glass filter preheated to 100° C. After removing the mother liquor, the crystallisate was washed with a total of 950 g of diethyl carbonate.
The solid was then blown dry with argon and vacuum dried at 100° C.
Yield: 124 g of white, coarsely crystalline salt (67% of theoretical)
Li$^+$: 5.25 mmol/g
Acid content: 5.7 μmol H$^+$/g LiBOB
Water content: 81 ppm (corresponding to 4 μmol/g LiBOB)
The product dissolved in PC and acetonitrile with very slight turbidity (less than 100 NTU).

The invention claimed is:
1. A solvent-free mixture of a crude lithium borate salt and lithium hydride, wherein the lithium hydride is at least 0.001 wt. % and at most 10 wt. %, relative to the weight of crude lithium borate salt, wherein the mixture has a water content of at most 100 μmol/g and an acid content of at most 10 μmol H$^+$/g of crude lithium borate salt.

2. A solvent-free mixture according to claim 1, wherein the lithium hydride is present in powder form with an average particle size of at most 100 μm.

3. A solvent-free mixture according to claim 1, wherein crude lithium borate salts according to formula I or formula II

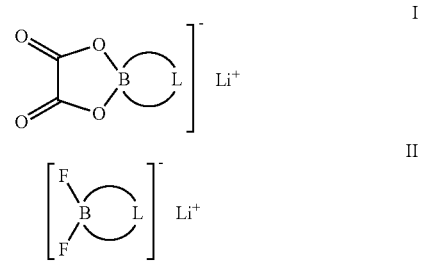

are used, wherein L is a chelating agent having two terminal oxygen atoms of formula

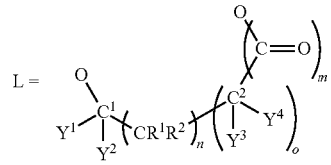

and wherein
Y$^1$ and Y$^2$ together denote 0, where m=0 or 1, n=0 or 1, o=0 and R$^1$ and R$^2$ independently of one another denote H, F, Cl, Br, OR (R=alkyl) or R' (alkyl), or
Y$^1$, Y$^2$, Y$^3$, Y$^4$ independently of one another each denote OR (R=alkyl), H, F, Cl, Br, R' (alkyl), where m=0 or 1, n=0, o=1, or
Y$^1$, C$^1$, Y$^3$ and C$^2$ are members of a 5- or 6-membered aromatic or heteroaromatic ring with at least one of N, O or S as a heteroelement, which can optionally be substituted with alkyl, alkoxy, carboxy or nitrile, wherein Y$^2$ and Y$^4$ are omitted, with n=0 and m=0 or 1, o=1.

4. A solvent-free mixture according to claim 1, wherein the crude lithium borate salt is selected from the group comprising lithium bis(oxalato)borate, lithium malonato-oxalatoborate, lithium glycolato-oxalatoborate, lithium salicylate-oxalatoborate, lithium lactato-oxalatoborate, lithium catecholato-oxalatoborate, lithium difluorooxalatoborate, lithium difluoro-malonatoborate, lithium difluoro-glycolatoborate, lithium difluoro salicylatoborate, lithium difluorolactatoborate, lithium difluorocatecholatoborate.

5. A process for producing a solvent-free mixture of lithium borate salts and lithium hydride wherein the lithium hydride is at least 0.001 wt. % and at most 10 wt. %, wherein the mixture has a water content of at most 100 μmol/g and an acid content of at most 10 μmol H$^+$/g of lithium borate salt as in claim 1, the process comprising
contacting a crude lithium borate salt in solid form or in suspension with an aprotic solvent or solvent blend which does not dissolve the crude lithium borate salt and the lithium hydride, and
removing the aprotic solvent or solvent blend to form a mixture of lithium borate salt and lithium hydride, either by distillation or by mechanical solid/liquid separation.

6. A process according to claim 5, wherein the removing of the aprotic solvent or solvent blend is by distillation under reduced pressure.

7. A process for producing a solution of a lithium borate salt, which process comprises contacting
- a solvent-free mixture of a crude lithium borate salt and lithium hydride, wherein the lithium hydride is at least 0.001 wt. % and at most 10 wt. %, relative to the weight of the crude lithium borate salt, wherein the mixture has a water content of at most 100 μmol/g and an acid content of at most 10 μmol H$^+$/g of crude lithium borate salt, with
- an aprotic solvent or solvent blend containing at least one aprotic solvent which dissolves the crude lithium borate salt, the crude lithium borate salt being dissolved therein,
- wherein the solution comprises a lithium borate salt in the aprotic solvent or solvent blend, wherein the lithium borate salt has a concentration of at least 1 wt. % and at most 50 wt. %, water is at most 100 μmol/g and acids are at most 10 μmol H$^+$ per g of dissolved lithium borate salt.

8. A process according to claim 7, wherein undissolved residues are removed by a solid/liquid separation operation.

9. A process for producing a solution of lithium borate salt in an aprotic solvent or solvent blend according to claim 7, further comprising removing undissolved residues by either filtration or centrifugation.

10. A process according to claim 9, wherein the removing is by membrane filtration, through a filter medium having a pore size of less than 0.5 μm.

11. A process for producing a lithium borate salt from solutions according to claim 7, wherein the lithium borate salt is obtained from the solution by an operation selected from total evaporation, displacement crystallisation, and evaporative crystallisation and wherein the lithium borate salt is isolated in solid form.

12. A process according to claim 7, wherein as crude lithium borate salts according to formula I or formula II

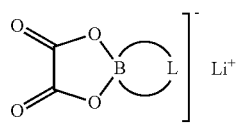  I

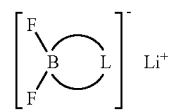  II are used, wherein L is a chelating agent having two terminal oxygen atoms of formula

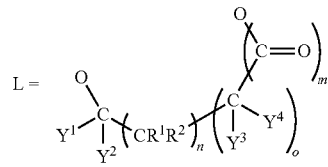

and wherein
- $Y^1$ and $Y^2$ together denote 0, where m=0 or 1, n=0 or 1, o=0 and $R^1$ and $R^2$ independently of one another denote H, F, Cl, Br, OR (R=alkyl) or R' (alkyl), or
- $Y^1$, $Y^2$, $Y^3$, $Y^4$ independently of one another each denote OR (R=alkyl), H, F, Cl, Br, R' (alkyl), where m=0 or 1, n=0, o=1, or
- $Y^1$, $C^1$, $Y^3$ and $C^2$ are members of a 5- or 6-membered aromatic or heteroaromatic ring with at least one of N, O or S as a heteroelement, which can optionally be substituted with alkyl, alkoxy, carboxy or nitrile, wherein $Y^2$ and $Y^4$ are omitted, with n=0 and m=0 or 1, o=1.

13. A process according to claim 7, wherein the aprotic solvent or solvent blend which dissolves the crude lithium borate salt contains ethers, ketones, carbonic acid esters, carboxylic acid esters, γ-lactones and/or nitriles or consists thereof.

14. A process according to claim 7, wherein the aprotic solvent or solvent blend which dissolves the crude lithium borate salt contains a hydrocarbon.

15. A process according to claim 7, wherein the aprotic solvent or solvent blend which dissolves the crude lithium borate salt is selected from the group comprising ethylene carbonate, propylene carbonate, butylene carbonate, γ-butyrolactone or γ-valerolactone.

* * * * *